United States Patent [19]

Nunn et al.

[11] 4,178,589

[45] Dec. 11, 1979

[54] THUMB-SUCKING ALARM SYSTEM

[75] Inventors: Robert G. Nunn, 6416 E. Lake Dr., San Diego, Calif. 92119; Louis M. Frank, Sunnyvale, Calif.; Ronald G. Bittle, 108 Peach Dr., Anna, Ill. 62906

[73] Assignees: Robert Gregory Nunn, Evanston; Ronald G. Bittle, Anna, both of Ill.; part interest to each

[21] Appl. No.: 889,278

[22] Filed: Mar. 23, 1978

[51] Int. Cl.² ............................................ G08B 21/00
[52] U.S. Cl. .................................. 340/573; 35/29 E; 200/DIG. 2; 200/61.05; 340/604
[58] Field of Search ............... 340/573, 604; 128/2 R; 200/DIG. 2, 61.05; 35/29 E

[56] References Cited

U.S. PATENT DOCUMENTS

| | | | |
|---|---|---|---|
| 2,812,757 | 11/1957 | Lusk et al. | 340/573 |
| 3,597,729 | 8/1971 | Lopez | 340/514 |
| 3,696,357 | 10/1972 | Kilgore | 340/573 |
| 4,069,817 | 1/1978 | Fenole et al. | 340/573 |

*Primary Examiner*—Glen R. Swann, III
*Attorney, Agent, or Firm*—Ronald A. Sandler

[57] ABSTRACT

A thumb-sucking alarm system includes a pair of spaced-apart sensor electrodes carried on a moisture-accepting portion of a flexible sensor tape adapted to be wrapped around the user's thumb, the electrodes being respectively connected to conductive lead strips on an elongated coupling portion of the tape, the distal end of which is wrapped around a plug for insertion into a mating receptacle in a housing adapted to be secured by a strap around the user's wrist. The conductive strips contact terminals of a battery-powered transistorized alarm circuit in the housing which generates an audible alarm signal in response to establishment of an electrical path between the electrodes by the moisture in a user's mouth when he sucks his thumb. A test button is provided on the housing for testing the audible signal generating circuit.

6 Claims, 8 Drawing Figures

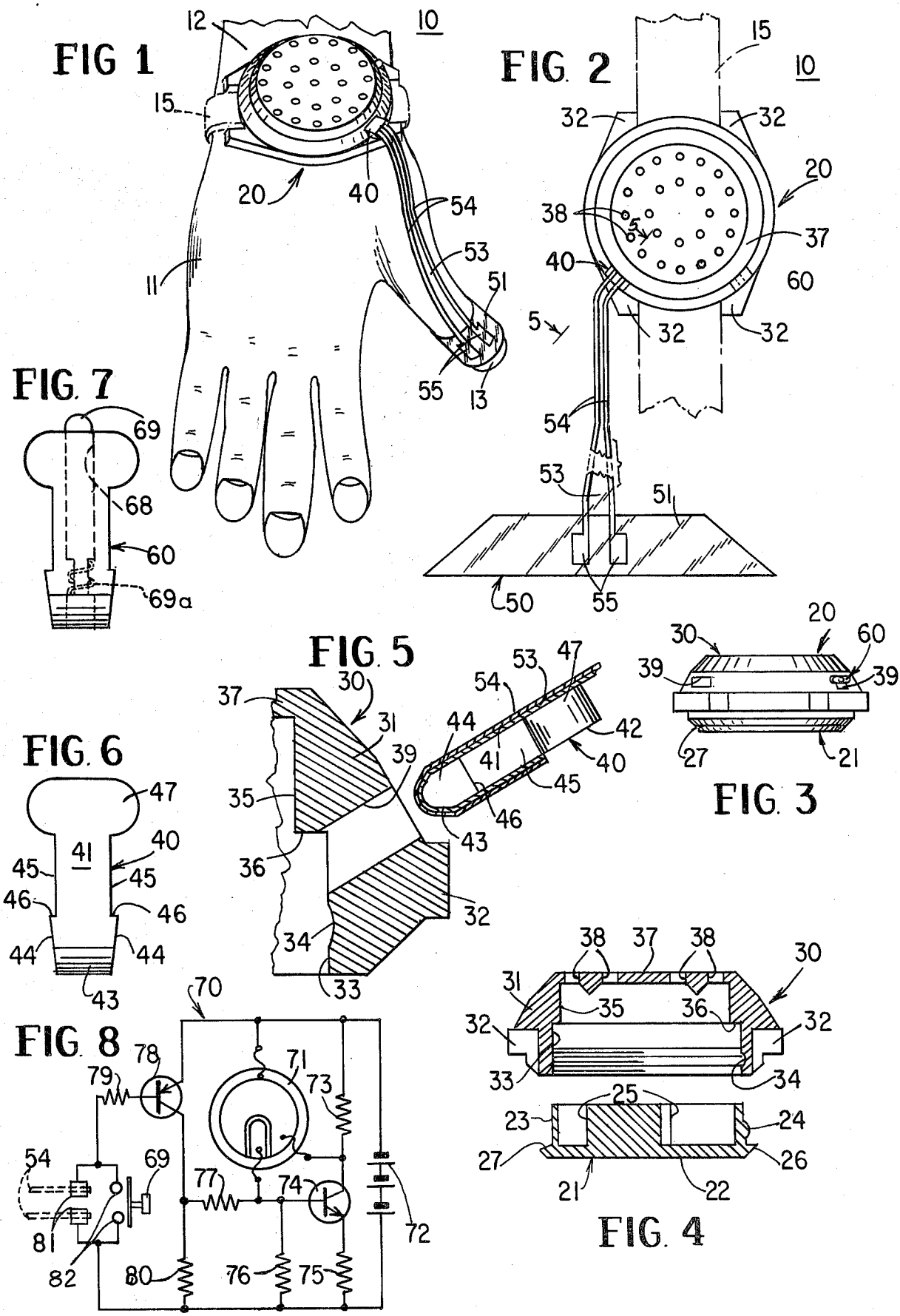

THUMB-SUCKING ALARM SYSTEM

BACKGROUND OF THE INVENTION AND PRIOR ART STATEMENT

The present invention relates to a training device and, more particularly, to a device for training an individual to break the habit of thumb sucking.

It is well known that habitual thumb sucking in children can result in deformation or irregularities of the teeth, resulting in abnormal tooth development and possibly malformation of facial features. Furthermore, when the habit of thumb sucking is continued into a child's school-age years it is usually a source of severe social stigma and may cause inferiority behavior and have a profound effect on a person's social adjustment.

Accordingly, many types of devices have been utilized in the past for attachment of the thumb of a thumb-sucking individual in an attempt to render thumb sucking distasteful or unsatisfying. One such device is disclosed in U.S. Pat. No. 3,334,625, issued to W. Baron on Aug. 8, 1967, which shows a device designed to prevent the creation of the usual vacuum in the mouth of the user, thereby eliminating one of the oral satisfactions normally associated with thumb sucking.

The present invention is related to a different type of therapeutic technique aimed at alerting the patient each time he sucks his thumb, to call it to his attention. Such a technique has been used in the past for toilet training and the treatment of chronic nocturnal enuresis, devices for which applications of such technique are disclosed in U.S. Pat. No. 3,530,855, issued to G. H. Balding on Sept. 29, 1970, and U.S. Pat. No. 3,592,195, issued to R. K. Van Wagenen et al. on July 13, 1972. These devices give an audible alarm signal in response to the presence of urine on a moisture sensor. A similar type of device is disclosed in U.S. Pat. No. 3,460,123, issued to J. V. Bass on Aug. 5, 1969.

A copy of each of the aforementioned prior art patents is filed herewith. Applicant is aware of no prior art device for applying this training technique to the treatment of thumb sucking.

SUMMARY OF THE INVENTION

The present invention provides a thumb-sucking alarm system which permits treatment of chronic thumb sucking by a training technique whereby, each time the patient sucks his thumb, he is alerted to that fact.

It is a general object of this invention to provide an economical alarm system, portable with the user, and responsive to thumb sucking for producing an alarm signal or indication.

A more particular object of this invention is the provision of an alarm system of the type set forth which is electronically operated and produces an audible alarm signal.

Still another object of this invention is the provision of an alarm system of the type set forth, which includes disposable moisture-responsive sensing means adapted to be secured to the user's thumb.

Another object of this invention is the provision of an alarm system of the type set forth, which includes means for selectively testing the operability of the alarm signal generator.

In summary, these objects are achieved by providing a thumb-sucking alarm system comprising moisture-detecting means portable with the body of a user and including sensing means adapted to be secured to a thumb of the user for disposition in the user's mouth when the user sucks the thumb, the moisture-detecting means being responsive to the presence of moisture on the sensing means for producing an output signal, and indicator means coupled to the moisture-detecting means and responsive to the output signal for producing an indication that the user is sucking his thumb.

Further features of the invention pertain to the particular arrangement of the parts of the thumb-sucking alarm system whereby the above-outlined and additional operating features thereof are attained.

The invention, both as to its organization and method of operation, together with further objects and advantages thereof, will best be understood by reference to the following specification taken in connection with the accompanying drawings.

BRIEF DESCRIPTION OF THE DRAWINGS

FIG. 1 is a perspective view of the alarm system of the present invention mounted on the hand of a user;

FIG. 2 is a fragmentary top plan view of the alarm system illustrated in FIG. 1;

FIG. 3 is an end elevational view of the housing of the alarm system illustrated in FIG. 2, as viewed from the lower end thereof;

FIG. 4 is an enlarged exploded view in vertical section of the two parts of the housing of FIG. 3;

FIG. 5 is a further enlarged fragmentary view in vertical section taken along the line 5—5 in FIG. 2, and illustrating the sensor tape plug and associated tape in position for insertion into the housing receptacle, the plug being illustrated in side elevation;

FIG. 6 is a front elevational view of the sensor plug illustrated in FIG. 5;

FIG. 7 is a front elevational view of the test plug of the present invention; and FIG. 8 is an electrical schematic circuit diagram of the alarm circuit of the present invention.

DESCRIPTION OF THE PREFERRED EMBODIMENT

Referring now to FIGS. 1 through 5 of the drawings, there is illustrated a thumb-sucking alarm system, generally designated by the numeral 10, which includes a housing, generally designated by the numeral 20, which is generally of the size and shape of a wristwatch and is adapted to be secured by a strap 15 to the wrist 12 of a user, in the same manner as a wristwatch.

The housing 20 preferably is formed of plastic and is of a two-part construction including a base 21 and a cover 30. The base 21 includes a circular bottom wall 22 and a cylindrical body portion integral with the bottom wall 22 and extending upwardly therefrom coaxially therewith, the cylindrical portion 23 having formed on the outer surface thereof a bead 24. Formed in the upper surface of the cylindrical portion 23 are a plurality of recesses or compartments 25 adapted to receive therein the components of an electrical alarm circuit 70 (see FIG. 8), in a suitable manner. The bottom wall 22 extends radially outwardly beyond the edges of the cylindrical portion 23 to form an annular flange 26 which is beveled as at 27 along a portion of the circumference thereof to form a grip for insertion of a fingernail or suitable tool, as will be explained more fully below.

The cover 30 includes a generally cylindrical side wall 31 provided with diametrically opposed pairs of circumferentially spaced-apart ears 32 extending outwardly therefrom for facilitating attachment to the strap 15. The cylindrical wall 31 has a large diameter cylindrical inner surface 33 provided with an indentation 34 therein and connected at the upper end thereof by a horizontal annular shoulder 36 to a small diameter inner surface 35. The upper end of the cylindrical side wall 31 is closed by a circular top wall 37 provided with a plurality of circular holes or apertures 38 formed therethrough and arranged in concentric rings of circumferentially spaced-apart holes (see FIG. 2). Respectively extending generally radially through the cylindrical side wall 31 adjacent to the ears 32 of one pair thereof are two downwardly inclined receptacle apertures 39, each of which is substantially rectangular in transverse cross section and provides communication between the inside and the outside of the housing 20.

The diameter of the inner surface 33 is very slightly greater than the outer diameter of the cylindrical portion 23 of the base 21 so that, in use, when the components of the circuit 70 have been assembled in the recesses 25 of the base 21, the cylindrical portion 23 thereof is received into the large diameter lower portion of the cover 30. The base 21 and cover 30 are thus pushed together to an assembled configuration, illustrated in FIG. 3, wherein the upper surface of the cylindrical portion 23 engages the shoulder 36 and the flange 26 engages the bottom edge of the cylindrical wall 31. The bead 24 cams past the lower edge of the cylindrical wall 31 and is received in the indentation 34 to provide a snap fit of the cover 30 over the base 21 firmly to hold the parts together. It will be noted that the beveled portion 27 of the flange 26 provides a slight gap between the flange 26 and the bottom of the cylindrical wall 31 to permit insertion of a fingernail or an appropriate tool to facilitate reopening of the housing 20.

Referring to FIG. 6, the alarm system 10 also includes a sensor plug, generally designated by the numeral 40, which is preferably integrally formed of plastic and includes spaced-apart parallel front and rear flat surfaces 41 and 42 interconnected at one end of the plug 40 by a tapered convex tip surface 43. The opposite side edges of the tip surface 43 and the adjacent portions of the front and rear surfaces 41 and 42 are interconnected by flat inclined end surfaces 44 which converge slightly toward the tip end of the sensor plug 43 and are respectively connected at the divergent ends thereof by short shoulder surfaces 46 to elongated parallel side surfaces 45, which are interconnected at the opposite end of the plug 40 by an enlarged generally oval-shaped head 47. The plug 40 is dimensioned to be received in one of the receptacle apertures 39 in the cover 30, the inclined end surfaces 44 being dimensioned to provide a wedge fit of the plug 40 into the receptacle aperture 39 to a fully inserted configuration, wherein the head 47 engages the outer surface of the cover side wall 31 and the arcuate tip surface 43 projects beyond the inner surface of the side wall 31.

The alarm system 10 also includes a sensor type, generally designated by the numeral 50, which is generally T-shaped and includes a generally trapezoidal thumb end 51 which forms the crossbar of the T and an elongated narrow coupling portion 53 integral with the thumb portion 51 and extending therefrom substantially normal thereto to form the post of the T. Preferably, the tape 50 is formed of a thin plastic material, which is of simple and inexpensive construction so that the sensor tape 50 may be disposable.

The thumb portion 51 is dimensioned to be wrapped around the tip of the user's thumb, with the ends of the thumb portion 51 overlapping and preferably being provided with adhesive patches securely to hold the thumb portion 51 in place. The coupling portion 53 has a length sufficient comfortably to reach the housing 20 mounted on the user's wrist, when the thumb portion 51 is secured to the user's thumb. Two parallel spaced-apart electrically conductive strips or leads 54 are formed on the coupling portion 53 and extend the length thereof, and are respectively connected to two spaced-apart rectangular electrodes carried by the thumb portion 51 in a moisture-accepting area centrally thereof.

Preferably, the width of the coupling portion 53 at the distal end thereof is equal to or less than the width of the sensor plug 40. In use, the tip of the coupling portion 53 is wrapped lengthwise around the sensor plug 40, as illustrated in FIG. 5, with the conductive strips 54 disposed on the outside. More particularly, the coupling portion 53 of the tape 50 extends downwardly along the front surface 41, around the arcuate tip surface 43 and then back up along the rear surface 42. When thus assembled, the sensor plug 40 with the tape 50 wrapped therearound are inserted into the appropriate one of the receptacle apertures 39, the sensor plug 40 and tape coupling portion 53 being dimensioned to accommodate such insertion. With the sensor plug 40 fully inserted in the aperture 39, the portions of the conductive strips 54 lying along the arcuate tip 43 will be respectively disposed for engagement with contacts of the circuit 70, as will be explained more fully below.

Referring to FIG. 7, the alarm system 10 also is provided with a test plug, generally designated by the numeral 60, which is substantially identical in construction with the sensor plug 40, with the exception that the test plug 60 is provided with a bore 68 extending longitudinally therethrough and receiving therein for movement axially thereof a test pin 69. Preferably, a compression spring 69a is retained in the bore 68 and resiliently urges the pin 69 to a normal rest position extending a predetermined distance outwardly beyond the head of the test plug 60. The test plug 60 is adapted to be received in the other one of the receptacle apertures 39 in the cover 30, in the same manner as was described above with respect to the sensor plug 40. When the test plug 60 is fully inserted into the associated receptacle aperture 39, it will be so positioned that when the pin 69 is depressed against the urging of the bias spring 69a, it will extend beyond the arcuate tip end of the test plug 60 for engagement with suitable test contacts of the circuit 70, as will be explained more fully below.

Referring now to FIG. 8 of the drawings, the alarm circuit 70 includes a piezoelectric transducer 71 which vibrates to produce an audible tone when suitable electric potentials are applied to the terminals thereof. The transducer 71 has three terminals, one of which is connected to the positive terminal of a three-cell battery 72, and is also connected via a resistor 73 to a second terminal of the transducer 71 and to the collector of a transistor 74, the emitter of which is connected via a resistor 75 to the negative terminal of the battery 72. The base of the transistor 74 is connected via a resistor 76 to the negative terminal of the battery 72, and is also connected to the third terminal of the transducer 71 and, via a resistor 77, to the collector of a transistor 78, the emitter of which is connected to the positive terminal of the battery 72. The base of the transistor 78 is connected via a resistor 79 and parallel sets of spaced-apart fixed contacts 81 and 82 to the negative terminal of the battery 72. The collector of the transistor 78 is also connected via a resistor 80 to the negative terminal of the battery 72.

The pairs of contacts 81 and 82 are respectively positioned in use adjacent to the inner ends of the receptacle apertures 39. Thus, when the sensor plug 40 and associated tape 50 are inserted into the corresponding receptacle aperture 39, the conductive strips 54 will respectively engage the sensor contacts 81. Similarly, when the test pin 69 is manually depressed, the inner end thereof will engage and bridge the test contacts 82.

In use, the transistor 74 cooperates with the piezoelectric transducer 71 to form an oscillator circuit, with the transducer 71 and the resistor 73 forming the collector load for the transistor 74, and the transducer 71 providing feedback to the base of the transistor 74. The bias of the transistor 74 is provided through the resistors 77 and 80, this bias being turned on and off by the transistor 78, the bias of which is determined by the resistor 79. The resistor 80, which serves as the collector load of the transistor 78, determines the value of sensor resistance at which the oscillations will start.

Thus, when moisture forms a conductive path between the electrodes 55, the resistance therebetween drops, and current begins to flow through the transistor 78. The resistor 80 is preferably of such a value that oscillations of the circuit 70 will start when the sensor resistance between the electrodes 55 drops to approximately 10 megohms, and full drive is obtained when the snesor resistance reaches 1 megohm or less. The resistor 76 stabilizes the D.C. operating point of the transistor 74 to insure startup of the oscillations. The transistor 74 provides A.C. gain, while the transistors 78 and 74 both provide D.C. amplification, the emitter resistor 75 of the transistor 74 providing both A.C. and D.C. gain stabilization therefor.

Thus, in use, the housing 20 is strapped to the user's wrist and the sensor tape 50 is applied to the user's thumb. Then, the coupling portion 53 of the tape 50 is wrapped around the sensor plug 40, which is inserted into the associated one of the receptacle apertures 39 for connecting the conductive strips 54 to the contacts 81. The circuit may be tested by depressing the test pin 69 of the test plug 60. Preferably, the thumb portion 51 of the tape 50 is so applied to the user's thumb that the electrodes 55 overlie the user's thumbnail so that, in the nomral thumb-sucking position, they will engage the user's tongue to facilitate bridging the electrodes 55 with a conductive path of moisture. The formation of such a conductive path on the moisture-accepting portion of the tape 50 completes the base circuit of the transistor 78 causing it to conduct, thereby turning on the bias of the transistor 74 and causing oscillations to begin for actuating the transducer 71 and producing an audible alarm signal, the holes 38 in the housing cover 30 enhancing audibility of this alarm signal.

It is a significant feature of the present invention that the sensor tape 50 is disposable for reasons of sanitation and the like. Thus, after use, the sensor plug 40 is removed from the receptacle 38 and the thumb portion 51 is removed from the user's thumb 13, whereupon the sensor tape 50 may be discarded and replaced with a new tape for the next application.

Preferably, the interconnections between the elements of the circuit 70 are printed on a printed circuit board, with the larger elements including the transducer 71, battery 72 and transistors 74 and 78 being received in the recesses 25 in the housing base 21. Preferably, the battery 72 is a nine-volt battery and may be held in its recess 25 by the cover 30 against the urging of a suitable bias means such as a compression spring, to facilitate removal of the battery and replacement thereof.

In a constructional model of the present invention, the sensor tape 50 is about 3 mils thick and is formed of a polyester such as du Pont's Mylar; the electrodes 55 and conductive strips 54 being formed of a silver-based ink-silver epoxy such as Electrodag #415 SS fabricated by Achison Colloidal of Port Huron, Michigan. The transducer 71 is a Bender Linden P/N70054FB piezoelectric transducer, the transistor 74 is Motorola's 2N3904, while the transistor 78 is a Motorola 2N3906, the battery 72 preferably being an S76E silver oxide battery. The resistor 73 is 1 Kohms, the resistor 75 is 47 ohms, the resistor 76 is 47 Kohms, the resistors 77 and 79 are each 100 Kohms, and the resistor 80 is 3.3 Kohms.

While there has been described what is at present considered to be the preferred embodiment of the invention, it will be understood that various modifications may be made therein, and it is intended to cover in the appended claims all such modifications as fall within the true spirit and scope of the invention.

What is claimed is:

1. A thumb-sucking alarm system comprising a housing adapted to be secured to the wrist of a user, signal-generating means disposed in said housing, sensing means coupled to said signal-generating means and adapted to be secured to a thumb of the user for disposition in the user's mouth when the user sucks the thumb, said signal-generating means being responsive to the presence of moisture on said sensing means for producing an output signal, alarm means mounted in said housing and coupled to said signal-generating means and responsive to said output signal for producing an audible alarm indicating that the user is sucking his thumb, said sensing means being disposable and including an elongated flexible tape provided at one end thereof with a moisture-accepting portion adapted to be secured in use on the thumb of a user, a pair of electrodes spaced apart on said moisture-accepting portion, a pair of electrical conductor leads respectively connected to said electrodes and insulated from each other and extending the length of said tape to the other end thereof, and means releasably coupling said other end of said tape to said housing with the adjacent ends of said lead conductors electrically connected to said signal-generating means, said signal-generating means being operable to produce said output signal in response to the establishment of a low-resistance path by moisture on said moisture-accepting portion between said electrodes when the user sucks the thumb.

2. The thumb-sucking alarm system set forth in claim 1, wherein said housing is provided with a socket therein, said releasable coupling means comprising a plug member adapted to receive said other end of said tape therearound and to be matably accepted in said socket.

3. The thumb-sucking alarm system set forth in claim 1, wherein said tape is integrally formed of a thin sheet of vinyl plastic, said electrodes and said electrical conductor leads comprising metallic portions imprinted on said tape.

4. A disposable sensing means for use in a thumb-sucking alarm system including alarm-signal-generating means, said sensor comprising an elongated flexible tape provided at one end thereof with a moisture-accepting portion adapted to be secured in use on the thumb of a user, a pair of electrodes spaced apart on said moisture-accepting portion, a pair of electrical conductor leads respectively connected to said electrodes and insulated from each other and extending the length of said tape to the other end thereof, said other end of said tape being adapted for electrical connection of the adjacent ends of said electrical conductor leads to the associated alarm-signal-generating means while the moisture-accepting portion is secured to the user's thumb for producing an alarm signal in response to the establishment of a low-resistance path by moisture on said moisture-accepting portion between said electrodes when the user sucks the thumb.

5. The sensor set forth in claim 4, wherein said tape is formed of polyester.

6. The sensor set forth in claim 4, wherein said tape is formed of polyester, said electrodes and said conductor leads being a silver-based ink-and-silver epoxy adhered to said tape.

* * * * *